(12) United States Patent
Chapman et al.

(10) Patent No.: US 11,344,057 B2
(45) Date of Patent: May 31, 2022

(54) CAPSULE-CONTAINING POUCHED PRODUCT FOR ORAL USE

(71) Applicant: R. J. Reynolds Tobacco Company, Winston-Salem, NC (US)

(72) Inventors: Paul Stuart Chapman, Winston-Salem, NC (US); David Troy Turfler, Collierville, TN (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 17/363,174

(22) Filed: Jun. 30, 2021

(65) Prior Publication Data
US 2022/0030928 A1 Feb. 3, 2022

Related U.S. Application Data

(63) Continuation of application No. 14/561,736, filed on Dec. 5, 2014.

(51) Int. Cl.
| | |
|---|---|
| *A24B 13/00* | (2006.01) |
| *A24B 15/16* | (2020.01) |
| *A24B 15/40* | (2006.01) |
| *A24B 15/30* | (2006.01) |
| *A24B 15/42* | (2006.01) |
| *A61K 9/00* | (2006.01) |
| *A61K 31/465* | (2006.01) |
| *A61K 47/38* | (2006.01) |
| *A61K 31/522* | (2006.01) |
| *A61K 31/125* | (2006.01) |
| *A61K 31/7004* | (2006.01) |
| *A61K 31/05* | (2006.01) |
| *A61K 31/198* | (2006.01) |
| *A61K 31/194* | (2006.01) |
| *A61K 31/191* | (2006.01) |
| *A61K 31/20* | (2006.01) |
| *A61K 31/4015* | (2006.01) |
| *A61K 31/375* | (2006.01) |
| *A61K 31/122* | (2006.01) |
| *A61K 31/352* | (2006.01) |
| *A61K 36/9068* | (2006.01) |
| *A61K 36/889* | (2006.01) |
| *A61K 36/8962* | (2006.01) |
| *A61K 36/16* | (2006.01) |
| *A61K 36/07* | (2006.01) |
| *A61K 36/45* | (2006.01) |
| *A61K 36/28* | (2006.01) |
| *A61K 36/38* | (2006.01) |
| *A61K 36/752* | (2006.01) |

(Continued)

(52) U.S. Cl.
CPC .............. *A24B 13/00* (2013.01); *A24B 15/16* (2013.01); *A24B 15/283* (2013.01); *A24B 15/303* (2013.01); *A24B 15/403* (2013.01); *A24B 15/42* (2013.01); *A61K 9/009* (2013.01); *A61K 31/05* (2013.01); *A61K 31/122* (2013.01); *A61K 31/125* (2013.01); *A61K 31/191* (2013.01); *A61K 31/194* (2013.01); *A61K 31/198* (2013.01); *A61K 31/20* (2013.01); *A61K 31/352* (2013.01); *A61K 31/375* (2013.01); *A61K 31/4015* (2013.01); *A61K 31/465* (2013.01); *A61K 31/522* (2013.01); *A61K 31/7004* (2013.01); *A61K 36/07* (2013.01); *A61K 36/16* (2013.01); *A61K 36/28* (2013.01); *A61K 36/38* (2013.01); *A61K 36/45* (2013.01); *A61K 36/67* (2013.01); *A61K 36/752* (2013.01); *A61K 36/82* (2013.01); *A61K 36/889* (2013.01); *A61K 36/8962* (2013.01); *A61K 36/9068* (2013.01); *A61K 47/38* (2013.01); *A61K 2236/331* (2013.01); *A61K 2236/333* (2013.01)

(58) Field of Classification Search
CPC ....... A24B 13/00; A24B 15/16; A24B 15/283; A24B 15/303; A24B 15/403; A24B 15/42; A61K 9/009; A61K 31/05; A61K 31/122; A61K 31/125; A61K 31/191; A61K 31/194; A61K 31/198; A61K 31/20; A61K 31/352; A61K 31/375; A61K 31/4015; A61K 31/465; A61K 31/522; A61K 31/7004; A61K 36/07; A61K 36/16; A61K 36/28; A61K 36/38; A61K 36/45; A61K 36/67; A61K 36/752; A61K 36/82; A61K 36/889; A61K 36/8962; A61K 36/9068; A61K 47/38; A61K 2236/331; A61K 2236/333
See application file for complete search history.

(56) References Cited

U.S. PATENT DOCUMENTS

| | | | |
|---|---|---|---|
| 8,067,046 B2 * | 11/2011 | Schleef .................. | A23L 33/21 426/78 |
| 2008/0317911 A1 * | 12/2008 | Schleef .................. | A23L 33/21 426/103 |
| 2021/0169790 A1 * | 6/2021 | Johnson ................. | A61K 47/06 |

* cited by examiner

*Primary Examiner* — Aaron J Kosar
(74) *Attorney, Agent, or Firm* — Womble Bond Dickinson (US) LLP

(57) ABSTRACT

A pouched product adapted for release of a releasable component therefrom is provided herein. The pouched product can include a water-permeable fabric pouch formed so as to define a cavity therein, and a composition contained within the cavity of the water-permeable fabric pouch, the composition including one or more releasable components that are released from the composition under mouth conditions and that are capable of movement through the water-permeable fabric pouch. The composition includes nicotine and at least one particulate non-tobacco material. The pouched product also includes at least one capsule contained within the cavity of the water-permeable fabric pouch, the capsule having a capsule wall surrounding an inner payload comprising at least one botanical.

23 Claims, 6 Drawing Sheets

(51) Int. Cl.
*A61K 36/67* (2006.01)
*A61K 36/82* (2006.01)
*A24B 15/28* (2006.01)

CAPSULE-CONTAINING POUCHED PRODUCT FOR ORAL USE

FIELD OF INVENTION

The present disclosure relates to products made or derived from tobacco, or that otherwise incorporate tobacco, and are intended for human consumption. In particular, the disclosure relates to a fleece that may be combined with smokeless tobacco to form a pouched product suitable for oral use.

BACKGROUND

Various products intended for oral use employ moisture permeable pouches or sachets. See for example, the types of representative smokeless tobacco products, as well as the various smokeless tobacco formulations, ingredients and processing methodologies, referenced in the background art set forth in U.S. Pat. Pub. Nos. 2011/0303511 to Brinkley et al. and 2013/0206150 to Duggins et al.; which are incorporated herein by reference. During use, such pouches or sachets are inserted into the mouth of the user, and water soluble components contained within those pouches or sachets are released as a result of interaction with saliva.

Products commonly referred to as "snus," for example, comprise ground tobacco materials incorporated within sealed pouches. Representative types of snus products have been manufactured in Europe, particularly in Sweden, by or through companies such as Swedish Match AB (e.g., for brands such as General, Ettan, Goteborgs Rape and Grovsnus); Fiedler & Lundgren AB (e.g., for brands such as Lucky Strike, Granit, Krekt and Mocca); JTI Sweden AB (e.g., for brands such as Gustavus) and Rocker Production AB (e.g., for brands such as Rocker). Other types of snus products have been commercially available in the U.S.A. through companies such as Philip Morris USA, Inc. (e.g., for brands such as Marlboro Snus); U.S. Smokeless Tobacco Company (e.g., for brands such as SKOAL Snus) and R. J. Reynolds Tobacco Company (e.g., for brands such as CAMEL Snus). See also, for example, Bryzgalov et al., 1N1800 Life Cycle Assessment, Comparative Life Cycle Assessment of General Loose and Portion Snus (2005); which is incorporated herein by reference.

Various types of snus products, as well as components for those products and methods for processing components associated with those products, have been proposed. See, for example, U.S. Pat. No. 8,067,046 to Schleef et al. and U.S. Pat. No. 7,861,728 to Holton, Jr. et al.; US Pat. Pub. Nos. 2004/0118422 to Lundin et al.; 2008/0202536 to Torrence et al.; 2009/0025738 to Mua et al.; 2011/0180087 to Gee et al.; 2010/0218779 to Zhuang et al.; 2010/0294291 to Robinson et al.; 2010/0300465 to Zimmermann; 2011/0061666 to Dube et al.; 2011/0303232 to Williams et al.; 2012/0067362 to Mola et al.; 2012/0085360 to Kawata et al.; 2012/0103353 to Sebastian et al. and 2012/0247492 to Kobal et al.; and PCT Pub. Nos. WO 05/063060 to Atchley et al. and WO 08/56135 to Onno; which are incorporated herein by reference. In addition, certain quality standards associated with snus manufacture have been assembled as a so-called GothiaTek standard. Furthermore, various manners and methods useful for the production of snus types of products have been proposed. See, for example, U.S. Pat. No. 4,607,479 to Linden and U.S. Pat. No. 4,631,899 to Nielsen; and US Pat. Pub. Nos. 2008/0156338 to Winterson et al.; 2010/0018539 to Brinkley et al.; 2010/0059069 to Boldrini; 2010/0071711 to Boldrini; 2010/0101189 to Boldrini; 2010/0101588 to Boldrini; 2010/0199601 to Boldrini; 2010/0200005 to Fallon; 2010/0252056 to Gruss et al.; 2011/0284016 to Gunter et al.; 2011/0239591 to Gruss et al.; 2011/0303511 to Brinkley et al.; 2012/0055493 to Novak III et al. and 2012/0103349 to Hansson et al.; and PCT Pub. Nos. WO 2008/081341 to Winterson et al. and WO 2008/146160 to Cecil et al.; which are incorporated herein by reference. Additionally, snus products can be manufactured using equipment such as that available as SB 51-1/T, SBL 50 and SB 53-2/T from Merz Verpackungmaschinen GmBH.

Certain types of products employing pouches or sachets that contain tobacco substitutes (or combinations of tobacco and tobacco substitutes) also have been proposed. See, for example, U.S. Pat. No. 5,167,244 to Kjerstad and U.S. Pat. No. 7,950,399 to Winterson et al.; and US Pat. Pub. Nos. 2005/0061339 to Hansson et al.; 2011/0041860 to Essen et al. and 2011/0247640 to Beeson et al.; which are incorporated herein by reference.

Certain types of product employing pouches or sachets have been employed to contain nicotine, such as those used for nicotine replacement therapy (NRT) types of products (e.g., a pharmaceutical product distributed under the tradename ZONNIC® by Niconovum AB). See also, for example, the types of pouch materials and nicotine-containing formulations set forth in U.S. Pat. No. 4,907,605 to Ray et al.; US Pat. Pub. Nos. 2009/0293895 to Axelsson et al. and 2011/0268809 to Brinkley et al.; and PCT Pub. Nos. WO 2010/031552 to Axelsson et al. and WO 2012/134380 to Nilsson; which are incorporated herein by reference.

Tobacco is known to include a number of constituents that may be more desirable or less desirable for release therefrom in a smokeless tobacco composition. It would be desirable to provide a smokeless tobacco product that is configured to alter the amount of certain constituents that may be released therefrom during use.

SUMMARY OF THE INVENTION

The present invention relates to products for oral delivery of one or more components of a composition. More particularly, a composition may be retained within a fleece—i.e., a water-permeable fabric—in the form of a pouch, and the delivery of the one or more components of the composition may be modified, such as to partially or substantially completely prevent release of one or more components from the fleece.

In some embodiments, the present disclosure relates to a pouched product. In particular, the pouched product can comprise a water-permeable fabric pouch formed so as to define a cavity therein. A composition can be contained within the cavity of the water-permeable fabric pouch, and the composition can comprise one or more releasable components that are released from the composition under mouth conditions and that are capable of movement through the water-permeable fabric pouch. A release modifying agent can also be included within the cavity or be otherwise combined with the water-permeable fabric, and the release modifying agent can be adapted to react with at least one of the one or more releasable components in the composition and thereby modify the release thereof from the water-permeable fabric pouch.

In various embodiments, the pouched product can be defined by one or more particular elements, characteristics, or functions. In particular, the pouched product can be further defined by one or more of the following descriptions in any combination.

The fabric pouch can be formed of a nonwoven web of fibers.

The fabric can comprise natural fibers.

The fabric can comprise synthetic fibers.

The fabric can comprise cellulosic fibers.

The fabric can comprise a heat sealable binder fiber.

The release modifying agent can form a part of the fabric.

The water-permeable fabric pouch can be infused with the release modifying agent.

The release modifying agent can be adsorbed or absorbed by at least a portion of the water-permeable fabric pouch.

The water-permeable fabric pouch can comprise a filter media.

The release modifying agent can be admixed with the composition contained within the cavity of the water-permeable fabric pouch.

The release modifying agent can be adapted to bind with at least one of the one or more releasable components in the composition so as to substantially prevent the release of at least a portion of the bound component from the water-permeable fabric pouch.

The release modifying agent can be in an encapsulated form.

The release modifying agent can be adapted to chemically or physically modify at least one of the one or more releasable components in the composition prior to or during release thereof from the water-permeable fabric pouch.

The release modifying agent can be adapted to react with a component selected from the group consisting of acetaldehyde, arsenic, benzo[a]pyrene, cadmium, crotonaldehyde, formaldehyde, nicotine, nicotine-derived nitrosamine ketone (NNK), N-nitrosonornicotine (NNN), derivatives thereof, decomposition products thereof, precursors thereof, and combinations thereof.

The release modifying agent can be selected from the group consisting of adsorbents, absorbents, molecularly imprinted polymers (MIPS), non-molecularly imprinted polymers (NIPS), botanicals, antioxidants, chelating agents, cyclodextrins, and combinations thereof.

The composition within the cavity of the water-permeable fabric pouch can comprise at least one of a particulate tobacco material, nicotine, particulate non-tobacco material treated to contain nicotine and/or flavoring agents, and fibrous plant material treated to contain a tobacco extract.

BRIEF DESCRIPTION OF THE DRAWINGS

Figure 1:
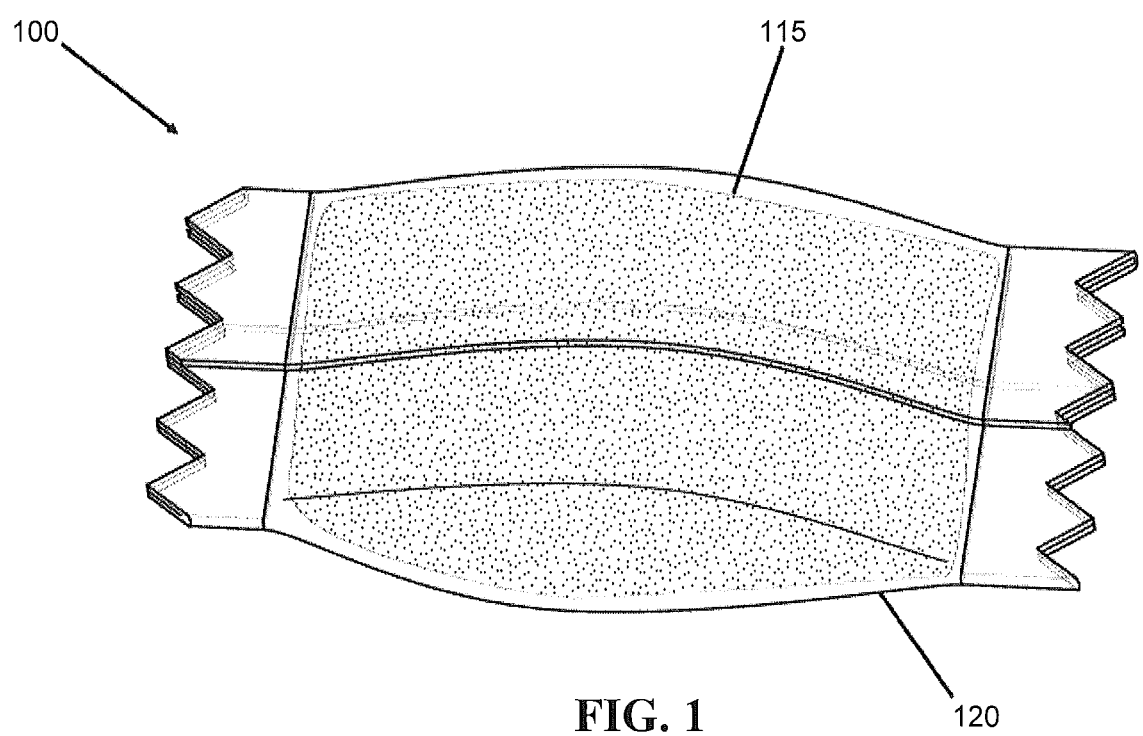
Figure 2:
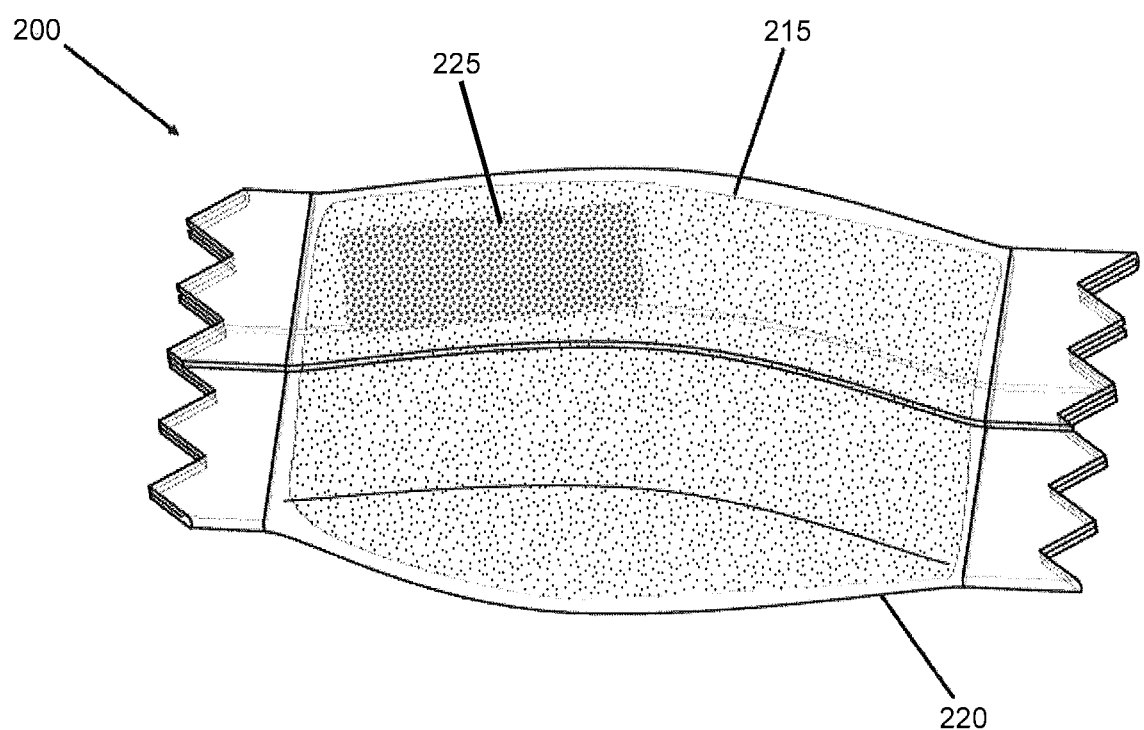
Figure 3:
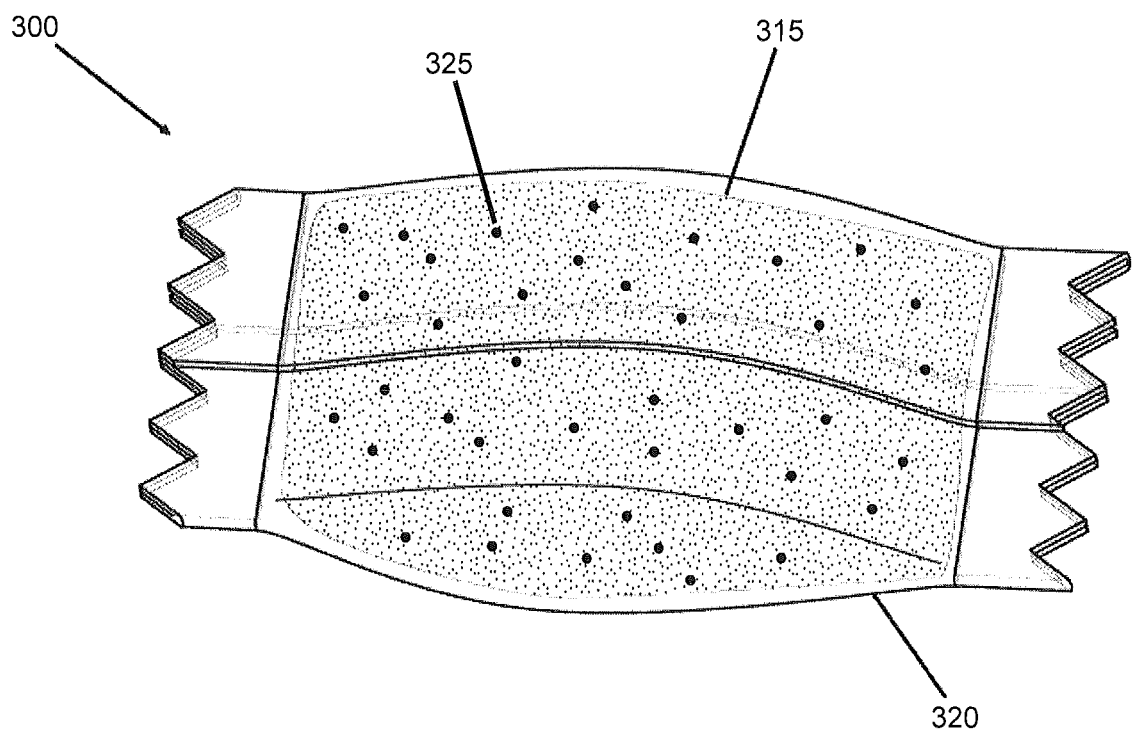
Figure 4:
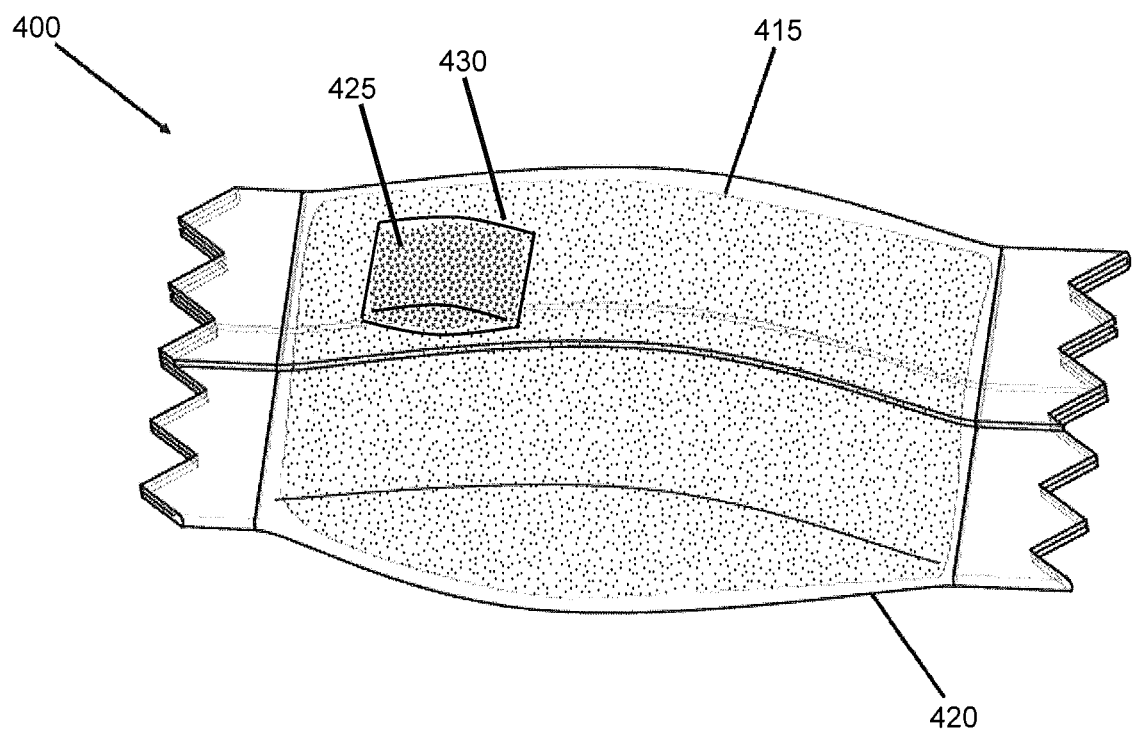
Figure 5A:
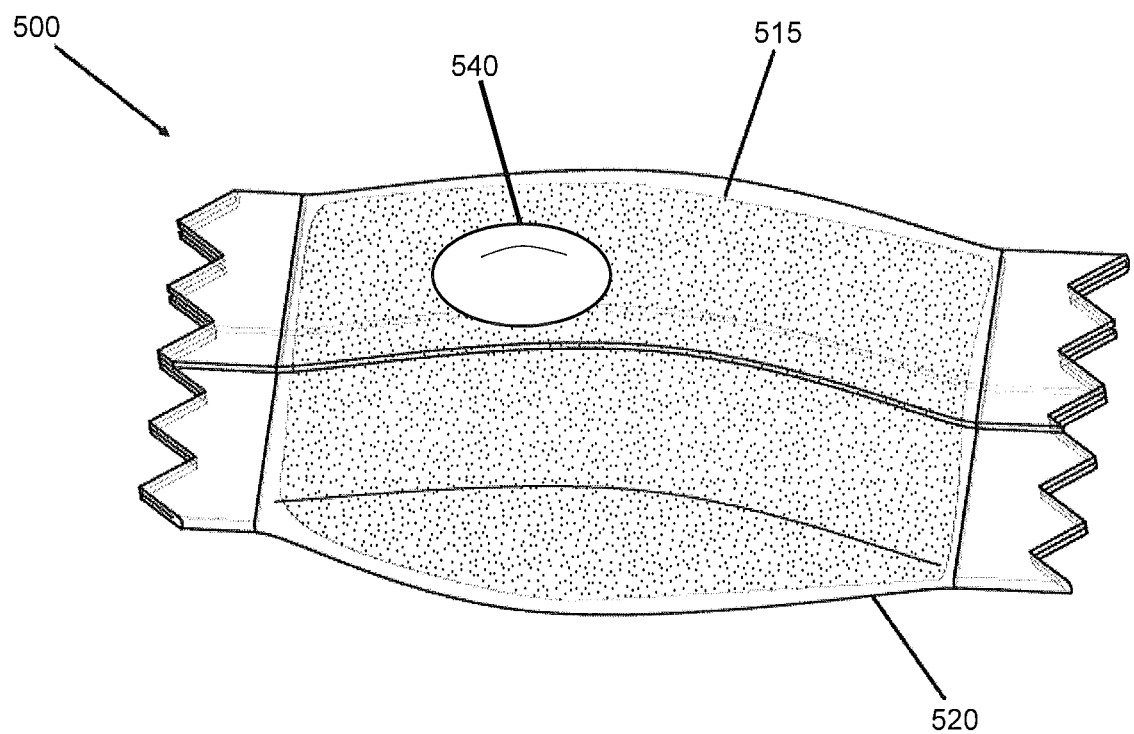
Figure 5B:
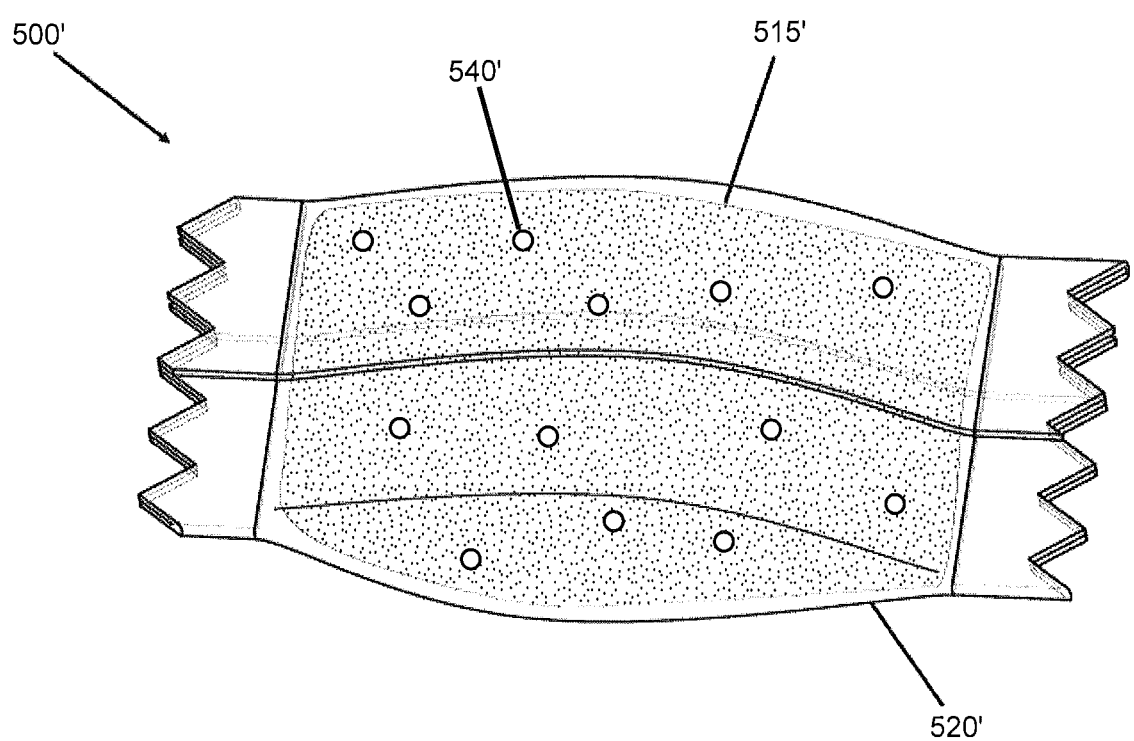

Having thus described the invention in the foregoing general terms, reference will now be made to the accompanying drawings, which are not necessarily drawn to scale, and wherein:

FIG. 1 is an illustration of a pouched product formed of a water-permeable fabric pouch having a composition therein according to an embodiment of the present disclosure;

FIG. 2 is an illustration of a pouched product formed of a water-permeable fabric pouch having a composition therein and including a release modifying agent according to an embodiment of the present disclosure;

FIG. 3 is an illustration of a pouched product formed of a water-permeable fabric pouch having a composition therein and including a release modifying agent in particulate form according to an embodiment of the present disclosure;

FIG. 4 is an illustration of a pouched product formed of a water-permeable fabric pouch having a composition therein and including a release modifying agent within a separate fleece container according to an embodiment of the present disclosure;

FIG. 5A is an illustration of a pouched product formed of a water-permeable fabric pouch having a composition therein and including an encapsulated release modifying agent according to an embodiment of the present disclosure; and FIG. 5B is an illustration of a pouched product formed of a water-permeable fabric pouch having a composition therein and including a plurality of capsules enclosing a release modifying agent according to an embodiment of the present disclosure.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

According to various embodiments of the present disclosure, a pouched product configured for insertion into the mouth of a user is provided. The pouched product can comprise a water-permeable fabric pouch as an outer element and a composition comprising one or more releasable components as an inner element. The water-permeable fabric pouch particularly can define a cavity in which the composition can be situated. The composition positioned within the pouch can be any composition containing one or more releasable components that are capable of movement through the water-permeable fabric pouch. Non-limiting, exemplary compositions include tea or coffee materials (e.g., in the context of a beverage pouch adapted for brewing or steeping) or compositions adapted for oral use (e.g., tobacco-derived products such as snus or nicotine replacement therapy products). In certain embodiments, the composition within the cavity of the pouch can comprise at least one of a particulate tobacco material, nicotine, particulate non-tobacco material (e.g., microcrystalline cellulose) treated to contain nicotine and/or flavoring agents, and fibrous plant material (e.g., beet pulp fiber) treated to contain a tobacco extract. In particular relation to compositions adapted for oral use, the releasable component in the composition can be a component that is released from the composition under mouth conditions.

Mouth conditions can encompass one or more characteristics (in any combination) associated with the presence of an item in the mouth of a user. For example, mouth conditions can include any combination of temperature, moisture, and pH typically found in the mouth of a human as well as the shear, compression, and other mechanical forces that may be applied by the teeth during chewing. Mouth conditions particularly can relate to being in contact with saliva. For example, saliva in the mouth may at least partially solubilize a releasable component so that the component is freed from the composition for potential movement through the water-permeable fabric pouch and into the mouth of the user. Mouth conditions can include conditions wherein a releasable component is solubilized in a solvent so as to be mobilized from the composition for free movement via the solvent, including movement through the fleece (i.e., the water-permeable fabric). As such, in some embodiments, mouth conditions can be viewed as a generic term whereby the pouched product is contacted with any aqueous solvent.

An exemplary embodiment of a pouched product 100 is shown in FIG. 1 and can comprise a water-permeable fabric 120 in the form of a pouch which contains a composition 115 adapted for oral use. The orientation, size, and type of the water-permeable fabric pouch and the type and nature of the composition adapted for oral use that are illustrated herein are not construed as limiting thereof.

In various embodiments, a moisture-permeable packet or pouch can act as a container for use of the composition within. The composition/construction of such packets or pouches, such as the water-permeable fabric pouch 120 in the embodiment illustrated in FIG. 1, may be varied as noted herein. For example, suitable packets, pouches, or containers of the type used for the manufacture of smokeless tobacco products, which can be suitable for use according to the present disclosure are available under the tradenames Catch-Dry, Ettan, General, Granit, Goteborgs Rape, Grovsnus White, Metropol Kaktus, Mocca Anis, Mocca Mint, Mocca Wintergreen, Kicks, Probe, Prince, Skruf, and TreAnkrare. A pouch type of product similar in shape and form to various embodiments of a pouched product described herein is commercially available as ZONNIC (distributed by Niconovum AB). Additionally, pouch type products generally similar in shape and form to various embodiments of a pouched product are set forth as snuff bag compositions E through J in Example 1 of PCT WO 2007/104573 to Axelsson et al., which is incorporated herein by reference, which are produced using excipient ingredients and processing conditions that can be used to manufacture pouched products as described herein.

In various embodiments of the present disclosure, a water-permeable fabric useful as a pouch to house a composition adapted for oral use can comprise a nonwoven web. During use, the user can place one pouched product containing the composition adapted for oral use in the mouth of the human subject/user. The mouth conditions, particularly contact with saliva, cause one or more components of the composition (i.e., a "releasable component") to be released from the composition. The releasable components preferably are capable of movement through the water-permeable fabric pouch and into the mouth of the user. The pouch preferably is not swallowed. The pouch may be subject to chewing but is preferably not chewed so as to substantially tear or otherwise perforate the pouch and allow the composition to spill into the mouth. The user is provided with flavor and satisfaction, and is not required to spit out any portion of the product. After a time suitable for use/enjoyment by the user (e.g., about 10 minutes to about 60 minutes, typically about 15 minutes to about 45 minutes), substantial amounts of the releasable components may be ingested by the human subject, and the pouch may be removed from the mouth of the human subject for disposal.

The pouch can be formed of any material that is suitable for use in the human mouth and that is sufficiently moisture-permeable, liquid-permeable, and/or water-permeable so as to allow for movement of the releasable components from the composition contained therein, particularly when in contact with saliva. As used herein, the term "water-permeable" particularly includes saliva-permeable.

The pouch material may be of a type that may be considered to be similar in character to the mesh-like type of material that is used for the construction of a tea bag. Components of the loosely arranged composition adapted for oral use readily diffuse through the pouch and into the mouth of the user (or into a surrounding environment, such as the fluid into which a pouched product may be placed, for example in embodiments wherein the pouched product may be a tea bag or the like). Preferred fabric materials for the pouched products may be designed and manufactured such that under conditions of normal use, a significant amount of the releasable components of the composition permeate through the pouch prior to the time that the pouch undergoes loss of its physical integrity. If desired, flavoring ingredients, disintegration aids, and other desired components, may be incorporated within, or applied to, the pouch material.

Various types of pouch materials and pouch manufacturing techniques are discussed in more detail below. The water-permeable fabric forming the pouch is generally suitable for containing, particularly in dry conditions, a composition that can be in a powdered, granular, shredded, or bulk solid form. The water-permeable fabric also preferably contains the composition under mouth conditions while allowing movement therethrough of the releasable components (i.e., the solubilized components) of the composition. In some embodiments, the water-permeable fabric may have a basic structure that is adapted to retain solids above a certain particle size while allowing particles below the defined size that may be dispersed in saliva, as well as solubilized components of the composition, to move therethrough.

The pouched products described herein particularly may include a composition adapted for oral use that is a tobacco-containing composition and/or a nicotine-containing pharmaceutical composition. That is, the composition adapted for oral use can be contained within a container, such as a pouch or bag, such as the type commonly used for the manufacture of snus types of products (e.g., a sealed, moisture permeable pouch that is sometimes referred to as a "portion").

Certain oral products of the disclosure will incorporate some form of a plant of the *nicotiana* species, and most preferably, those compositions or products incorporate some form of tobacco. The selection of the plant from the *nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *rustica* tobaccos, as well as various other rare or specialty tobaccos. Additional information on types of *nicotiana* species suitable for use in the present invention can be found in US Pat. Appl. Pub. No. 2012/0192880 to Dube et al., which is incorporated by reference herein.

The portion or portions of the plant of the *nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching, or otherwise subjected to storage or treatment for later use. Exemplary processing techniques are described, for example, in US Pat. Appl. Pub. Nos. 2009/0025739 to Brinkley et al. and 2011/0174323 to Coleman, III et al., which are incorporated by reference herein.

A harvested portion or portions of the plant of the *nicotiana* species can be physically processed. In certain embodiments, the tobacco material is used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like.

In certain embodiments, at least a portion of the tobacco material employed in the tobacco composition or product can have the form of an extract. Tobacco extracts can be obtained by extracting tobacco using a solvent having an aqueous character such as distilled water or tap water. As such, aqueous tobacco extracts can be provided by extracting tobacco with water, such that water insoluble pulp material is separated from the aqueous solvent and the water soluble and dispersible tobacco components dissolved and dispersed therein. Tobacco extraction techniques and tobacco extract processing techniques are described, for example, in US Pat. Pub. No. 2013/0312774 to Holton, Jr., which is incorporated by reference herein.

In certain embodiments, the pouched products of the invention can include a nicotinic compound. Various nicotinic compounds, and methods for their administration, are set forth in US Pat. Pub. No. 2011/0274628 to Borschke, which is incorporated herein by reference. As used herein, "nicotinic compound" or "source of nicotine" often refers to naturally-occurring or synthetic nicotinic compound unbound from a plant material, meaning the compound is at least partially purified and not contained within a plant structure, such as a tobacco leaf. Most preferably, nicotine is naturally-occurring and obtained as an extract from a *nicotiana* species (e.g., tobacco). The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis.

Nicotinic compounds can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotinic compound can be employed in the form of a resin complex of nicotine, where nicotine is bound in an ion exchange resin, such as nicotine polacrilex. See, for example, U.S. Pat. No. 3,901,248 to Lichtneckert et al., which is incorporated herein by reference. At least a portion of the nicotine can be employed in the form of a salt. Salts of nicotine can be provided using the types of ingredients and techniques set forth in U.S. Pat. No. 2,033,909 to Cox et al. and U.S. Pat. No. 4,830,028 to Lawson et al., and Perfetti, *Beitrage Tabakforschung Int.*, 12: 43-54 (1983), which are incorporated herein by reference. See, also, US Pub. No. 2011/0268809 to Brinkley et al., which is incorporated herein by reference. Additionally, salts of nicotine have been available from sources such as Pfaltz and Bauer, Inc. and K&K Laboratories, Division of ICN Biochemicals, Inc.

Representative types of excipients or other additional ingredients that are particularly useful for the manufacture of nicotine-containing products or tobacco-containing products include fillers or carriers for active ingredients (e.g., calcium polycarbophil, microcrystalline cellulose, cornstarch, beet pulp fiber, silicon dioxide or calcium carbonate), thickeners, film formers and binders (e.g., hydroxypropyl cellulose, hydroxypropyl methylcellulose, acacia, sodium alginate, xanthan gum and gelatin), buffers and pH control agents (e.g., magnesium oxide, magnesium hydroxide, potassium carbonate, sodium carbonate, potassium bicarbonate, sodium bicarbonate, or mixtures thereof), antiadherents (e.g., talc), glidants (e.g., colloidal silica), natural or artificial sweeteners (e.g., saccharin, acesulfame K, aspartame, sucralose, isomalt, lactose, mannitol, sorbitol, xylitol and sucrose), humectants (e.g., glycerin), preservatives and antioxidants (e.g., sodium benzoate and ascorbyl palmitate), surfactants (e.g., polysorbate 80), natural or artificial flavors (e.g., mint, cinnamon, cherry or other fruit flavors), dyes or pigments (e.g., titanium dioxide or D&C Yellow No. 10), and lubricants or processing aids (e.g., calcium stearate or magnesium stearate). Certain types of nicotine-containing products or tobacco-containing products also can have outer coatings composed of ingredients capable of providing acceptable outer coatings (e.g., an outer coating can be composed of ingredients such as carnauba wax, and pharmaceutically acceptable forms of shellacs, glazing compositions and surface polish agents). Adhesives, coatings, colorants, and other ingredients used in products described herein can be generally recognized as safe, non-toxic, ingestible and otherwise suitable for oral use.

Various combinations of materials, such as those described above, can be used in forming the composition that is contained within the cavity defined by the water-permeable fabric pouch. The composition thus can include a number of releasable components that are desired for release by the user into the user's mouth, such as flavor components and the like. Some compositions, however, can include releasable components that are desired to be partially, substantially completely, or completely prevented from release into the mouth under mouth conditions. In other words, although certain components may be released from a composition under mouth conditions, it may be desirable to modify the release of one or more of such components.

In various embodiments, a pouched product also can comprise a release modifying agent. In particular, a release modifying agent can be a material that is adapted to react with at least one of the releasable components in the composition that is positioned within the water-permeable fabric pouch and thereby modify the release thereof from the water-permeable fabric pouch.

In an example embodiment, a pouched product 200 is shown in FIG. 2 and can comprise a water-permeable fabric 220 in the form of a pouch which contains a composition 215 adapted for oral use. The pouched product 200 further includes a release modifying agent 225, which may be, for example, a particulate activated carbon or any further material as described herein.

A release modifying agent useful according to the present disclosure can be configured to modify the release of a releasable component in a variety of manners. For example, in some embodiments, a release modifying agent can be adapted to bind with a releasable component in the composition. In such embodiments, the release modifying agent can be associated with the water-permeable fabric pouch in a manner such that the release modifying agent is not substantially disassociated from the pouched product under mouth conditions (i.e., there is substantially no release from the pouch into the mouth). Exemplary associations between the release modifying agent and the water-permeable fabric pouch are further described below. Since the release modifying agent is substantially prevented from disassociating from the water-permeable fabric pouch, a releasable component that is bound by the release modifying agent is likewise substantially prevented from movement out of the water-permeable fabric pouch. By such binding, the release modifying agent prevents the release of at least a portion of the releasable component (i.e., the bound component) from the water-permeable fabric pouch.

A release modifying agent that is a binding agent may be configured to bind any percentage of the releasable component that may be released from the mass of the composition contained within the water-permeable fabric pouch up to 100% by weight of the releasable component. For example, a release modifying binding agent may be configured to bind about 1% to about 99.9%, about 10% to about 99.5%, or about 25% to about 99% by weight of the releasable component that is released from the composition under mouth conditions. The release modifying binding agent thus may be included in the pouched product in a mass sufficient to achieve the desired binding.

The binding achieved with a release modifying binding agent can be by one or more mechanisms. For example, the release modifying binding agent may be configured to physically bind the releasable component; the release modifying binding agent may be configured to covalently bond with the releasable component; the release modifying agent may be configured to ionically bond with the releasable component; the release modifying agent may be configured to undergo a further bond (e.g., hydrogen bonds and Van der Waals forces) with the releasable component.

In some embodiments, a release modifying agent can be adapted to chemically or physically modify a releasable component in the composition prior to or during release thereof from the water-permeable fabric pouch. The releasable component thus may be altered so that the material that ultimately does move through the water-permeable fabric pouch is in some way different from the releasable component that is initially released from the composition. For example, the release modifying agent may be an oxidizing agent or a reducing agent that oxidizes or reduces a releasable component so that at least a portion of the releasable component that is released into the mouth is in an oxidized form or a reduced form relative to the releasable component that is initially released from the composition within the water-permeable fabric pouch. As a further, non-limiting example, a release modifying agent may be configured as a decomposing agent and may at least partially decompose a releasable component. As still another non-limiting example, a release modifying agent may be configured as a bond cleaving agent that facilitates scission of a releasable component. As another non-limiting example, a release modifying agent may be configured as a derivatizing agent that reacts with the releasable component for form a derivative of the releasable component.

In some embodiments, a combination of release modifying agents may be used so that the release of multiple releasable components may be modified. A plurality of release modifying agents may separately modify the release of different releasable components (e.g., release modifying agent A modifying the release of releasable component X and release modifying agent B modifying the release of releasable component Y). As a non-limiting example, a plurality of binding agents can be used to bind, and thus modify the release of, a plurality of releasable components.

A plurality of release modifying agents may be used in combination to modify the release of the same releasable component. For example, a first release modifying agent may be adapted to chemically or physically modify a releasable component, and a second release modifying agent may be adapted to bind one or more materials representing the modifying releasable component (e.g., release modifying agent A' changing a releasable component X' into modified releasable components Z' and Z", one or both of which may be bound by release modifying agent B').

A release modifying agent may be incorporated into the pouched product in a variety of manners. In some embodiments, a release modifying agent can form at least a part of the water-permeable fabric. For example, the water-permeable fabric may be formed of a plurality of fibers, and the release modifying agent can be attached (e.g., covalently, ionically, or the like) to at least a portion of the fibers. As another non-limiting example, at least a portion of the fibers may be formed from a material that is a release modifying agent (e.g., a polymeric material). As still another non-limiting example, the water-permeable fabric pouch can be infused with the release modifying agent. In another non-limiting example, the release modifying agent can be adsorbed or absorbed by at least a portion of the water-permeable fabric pouch.

In some embodiments, a release modifying agent can be in a powdered or particulate form. The particulate release modifying agent may be adhered or otherwise attached to the water-permeable fabric. For example, in FIG. 2, the release modifying agent 225 may be a layer of particulate activated carbon adhered to the water permeable fabric 220. The particulate release modifying agent may be associated with the composition contained in the cavity of the water-permeable fabric pouch. For example, as seen in the pouched product 300 of FIG. 3, the particulate release modifying agent 325 may be admixed with the composition 315 within the water permeable fabric 320.

The water-permeable fabric may exhibit a porosity sufficiently sized to allow the releasable components to move therethrough under mouth conditions. Preferably, a particulate release modifying agent is sized so that the particles are substantially prevented from passing through the fabric. In some embodiments, particles of a release modifying agent may be provided in a separate pouch that can be included inside the water-permeable pouch. For example, as seen in the pouched product 400 of FIG. 4, the particulate release modifying agent 425 may be contained in a containment fleece 430 and positioned within the water permeable fabric 420 along with the composition 415 within.

In some embodiments, a release modifying agent can be in an encapsulated form. The capsule can comprise a capsule wall that is formed of a material that is configured to allow for dispersement of the release modifying agent under desired conditions. For example, the capsule wall may comprise a material that is configured to dissolve or otherwise degrade under mouth conditions. Preferably, the capsule is configured to disperse the release modifying agent sufficiently rapidly so as to modify the release of the releasable component from the composition in the water-permeable fabric pouch. As another non-limiting example, the capsule wall may comprise a material that is configured to be broken or otherwise degraded by shear forces (e.g., chewing). While suitable encapsulated materials may be described herein in relation to microcapsules, it is understood that such terminology is not intended to be viewed as limiting of the capsule sizes.

The crush strength of suitable microcapsules can be sufficient to allow for normal handling and storage without significant degree of premature or undesirable breakage. Providing capsules that possess both suitable integrity during storage and the ability to rupture or otherwise break down at the time of use can be determined by experimentation, depending upon factors such as capsule size and type, and is a matter of design choice. See, for example, U.S. Pat. Pub. No. 2007/0068540 to Thomas et al., which is incorporated herein by reference.

An exemplary capsule may include an outer shell incorporating a material such as wax, gelatin, cyclodextrin, or alginate, and an inner payload incorporating the release modifying agent, which may be particulate in some embodiments or may be an aqueous or non-aqueous liquid (e.g., a solution or dispersion of at least one release modifying agent within water or an organic liquid such as an alcohol or oil; or a mixture of water and a miscible liquid like alcohol or glycerin). Thus, for example, a plurality of such capsules may be incorporated within the pouch along with the composition to be retained therein; and during use of the product, a crushing or other destruction of the capsules may allow the capsules to release the additive contained therein.

The capsules used in the pouched product of the invention may be uniform or varied in size, weight, and shape. A representative capsule can be generally spherical in shape. However, suitable capsules may have other types of shapes, such as generally rectilinear, oblong, elliptical, or oval shapes. Exemplary microcapsules may have diameters of less than about 100 microns, such as microcapsules having diameters in the range of about 1 to about 40 microns, or about 1 micron to about 20 microns.

In some embodiments, larger capsules may be utilized. For example, a capsule utilized in the pouch product may have a size of about 0.5 mm to about 5 mm or about 0.6 mm to about 3 mm in diameter.

The number of capsules incorporated into the pouched product can vary, depending upon factors such as the size of the capsules, the character or nature of the additive in the payload, the desired attributes of the composition within the pouch and the desired release modification thereof, and the like. In some embodiments, only a single capsule may be included. For example, as seen in the pouched product 500 of FIG. 5A, a capsule 540 having the release modifying agent (not visible) provided therein may be positioned within the water permeable fabric 520 along with the composition 515 within. The single capsule 540 can thus be relatively large in size. In other embodiments, a plurality of capsules may be included. For example, as seen in the pouched product 500' of FIG. 5B, a plurality of capsules 540' each having the same or a different release modifying agent (not visible) provided therein may be positioned within the water permeable fabric 520' along with the composition 515' within. The plurality of capsules 540' can thus be relatively small in size. In particular, microcapsules may be used. The number of capsules incorporated within pouched product, for example, can exceed about 5, can exceed about 10, can exceed about 20, can exceed about 40, and can even exceed about 100. In certain embodiments, the number of capsules/microcapsules can be greater than about 500, and even greater than about 1,000.

The total weight of the capsules contained within the smokeless tobacco product may vary, but is typically greater than about 10 mg, often greater than about 20 mg, and can be greater than about 30 mg. The total weight of the capsules is typically less than about 200 mg, often less than about 100 mg, and can be less than about 50 mg.

The capsules can be formed using any encapsulating technology known in the art. For example, microcapsules can be formed using any of various chemical encapsulation techniques such as solvent evaporation, solvent extraction, organic phase separation, interfacial polymerization, simple and complex coacervation, in-situ polymerization, liposome encapsulation, and nanoencapsulation. Alternatively, physical methods of encapsulation could be used, such as spray coating, pan coating, fluid bed coating, annular jet coating, spinning disk atomization, spray cooling, spray drying, spray chilling, stationary nozzle coextrusion, centrifugal head coextrusion, or submerged nozzle coextrusion.

Regardless of the encapsulation methodology employed, the outer wall or shell material and solvents used to form the capsules can vary. Classes of materials that are typically used as wall or shell materials include proteins, polysaccharides, starches, waxes, fats, natural and synthetic polymers, and resins. Exemplary materials for use in the microencapsulation process used to form the microcapsules include gelatin, acacia (gum arabic), polyvinyl acetate, potassium alginate, carob bean gum, potassium citrate, carrageenan, potassium polymetaphosphate, citric acid, potassium tripolyphosphate, dextrin, polyvinyl alcohol, povidone, dimethylpolysiloxane, dimethyl silicone, refined paraffin wax, ethylcellulose, bleached shellac, modified food starch, sodium alginate, guar gum, sodium carboxymethylcellulose, hydroxypropyl cellulose, sodium citrate, hydroxypropylmethylcellulose, sodium ferrocyanide, sodium polyphosphates, locust bean gum, methylcellulose, sodium trimetaphosphate, methyl ethyl cellulose, sodium tripolyphosphate, microcrystalline wax, tannic acid, petroleum wax, terpene resin, tragacanth, polyethylene, xanthan gum, and polyethylene glycol.

Microcapsules are commercially available, and exemplary types of microcapsule technologies are of the type set forth in Gutcho, Microcapsules and Microencapsulation Techniques (1976); Gutcho, Microcapsules and Other Capsules Advances Since 1975 (1979); Kondo, Microcapsule Processing and Technology (1979); Iwamoto et al., AAPS Pharm. Sci. Tech. 2002 3(3): article 25; U.S. Pat. No. 3,550,598 to McGlumphy; U.S. Pat. No. 4,889,144 to Tateno et al.; U.S. Pat. No. 5,004,595 to Cherukuri et al.; U.S. Pat. No. 5,690,990 to Bonner; U.S. Pat. No. 5,759,599 to Wampler et al.; U.S. Pat. No. 6,039,901 to Soper et al.; U.S. Pat. No. 6,045,835 to Soper et al.; U.S. Pat. No. 6,056,992 to Lew; U.S. Pat. No. 6,106,875 to Soper et al.; U.S. Pat. No. 6,117,455 to Takada et al.; U.S. Pat. No. 6,325,859 to DeRoos et al.; U.S. Pat. No. 6,482,433 to DeRoos et al.; U.S. Pat. No. 6,612,429 to Dennen; and U.S. Pat. No. 6,929,814 to Bouwmeesters et al.; U.S. Pat. Appl. Pub. Nos. 2006/0174901 to Karles et al. and 2007/0095357 to Besso et al.; and PCT WO2007/037962 to Holton et al.; each of which is incorporated herein by reference. Suitable types of microcapsules are available from sources such as Microtek Laboratories of Dayton, Ohio. Exemplary types of commercially available microencapsulating techniques include those marketed under the trade names ULTRASEAL™ and PERMASEAL™ available from Givaudan headquartered in Vernier, Switzerland.

Representative types of capsules are of the type commercially available as "Momints" by Yosha! Enterprises, Inc. and "Ice Breakers Liquid Ice" from The Hershey Company. Representative types of capsules also have been incorporated in chewing gum, such as the type of gum marketed under the tradename "Cinnaburst" by Cadbury Adams USA. Representative types of capsules and components thereof also are set forth in U.S. Pat. No. 3,339,558 to Waterbury; U.S. Pat. No. 3,390,686 to Irby, Jr. et al.; U.S. Pat. No. 3,685,521 to Dock; U.S. Pat. No. 3,916,914 to Brooks et al.; U.S. Pat. No. 4,889,144 to Tateno et al. U.S. Pat. No. 6,631,722 to MacAdam et al.; and U.S. Pat. No. 7,115,085 to Deal; US Pat. Pub. Nos. 2004/0261807 to Dube et al.; 2006/0272663 to Dube et al.; 2006/01330961 to Luan et al.; 2006/0144412 to Mishra et al.; 2007/0012327 to Karles et al.; and 2007/0068540 to Thomas et al.; PCT WO 03/009711 to Kim; PCT WO2006/136197 to Hartmann et al.; PCT WO 2006/136199 to Mane et al., PCT WO 2007/010407; and PCT WO 2007/060543, as well as within filtered cigarettes that have been marketed under the tradename "Camel Lights with Menthol Boost" by R. J. Reynolds Tobacco Company, which are incorporated herein by reference. See also, the types of capsules and components thereof set forth in U.S. Pat. No. 5,223,185 to Takei et al.; U.S. Pat. No. 5,387,093 to Takei; U.S. Pat. No. 5,882,680 to Suzuki et al.; U.S. Pat. No. 6,719,933 to Nakamura et al. and U.S. Pat. No. 6,949,256 to Fonkwe et al.; and U.S. Pat. App. Pub. Nos. 2004/0224020 to Schoenhard; 2005/0123601 to Mane et al.; 2005/0196437 to Bednarz et al.; and 2005/0249676 to Scott et al.; which are incorporated herein by reference. The capsules may be colored, provided with smooth or rough surfaces, have rigid or pliant shells, have brittle or durable shells, or other desired features or characters.

Any material that will react with a releasable component as defined herein may be used as a release modifying agent. Preferably, the release modifying agent is formed of a material that is considered safe for oral use in humans and/or safe for ingestion by humans.

In some embodiments, a release modifying agent may be defined in relation to its reactivity with certain elements, molecules, compounds, or the like that may be present in, and releasable from, the composition included in the pouched product. Such reactivity may relate to binding (e.g., absorption, adsorption, covalent bonding) or a specific chemical reaction. As a non-limiting example a release modifying agent may be any material that is adapted to react with one or more of the following: acetaldehyde, arsenic, benzo[a]pyrene (BaP), cadmium, crotonaldehyde, formaldehyde, nicotine, nicotine-derived nitrosamine ketone (NNK), N-nitrosonornicotine (NNN), other tobacco-specific nitrosamines, derivatives thereof, decomposition products thereof, precursors thereof, and the like. A release modifying agent further may be any material that is adapted to react with a compound that is releasable from tobacco under mouth conditions. For exemplary compounds that are present in tobacco, see for example, Rodgman and Perfetti, The Chemical Components of Tobacco and Tobacco Smoke, CRC Press (2008). Further examples of molecules that may be releasable from tobacco under various conditions include the following: 1-aminonapthalene, 2-aminonapthalene, 3-aminobiphenyl, 4-aminobiphenyl, methyl ethyl ketone, acetone, acrolein, butyraldehyde, priopionaldehyde, catechol, hydroquinone, m-cresol, p-cresol, o-cresol, phenol, resorcinol, ammonia, hydrogen cyanide, nitric oxide, carbon monoxide, acrylonitrile, 1,3-butadiene, benzene, isoprene, toluene, styrene, pyridine, quinoline, chromium, lead, mercury, nickel, selenium, N'-nitrosoanabasine (NAB), N'-nitrosoanatabine (NAT), and tar. For additional compounds noted to be present in smokeless tobacco, see, for example, International Agency for Research on Cancer. Smokeless Tobacco and Some Tobacco-Specific N-Nitrosamines. Lyon, France: World Health Organization International Agency for Research on Cancer, IARC Monographs on the Evaluation of Carcinogenic Risks to Humans, Volume 89 (2007), which is incorporated herein by reference.

A release modifying agent also may be any material that is adapted to react with compounds that may be disadvantageously present in a portion of the tobacco seed, e.g., in tobacco seed oil, such as pesticides (e.g., herbicides, insecticides, or rodenticides), fertilizers, or residues thereof. Exemplary pesticides that can be targeted for release modification include, but are not limited to, ethion, parathion, diazinon, methyl parathion, thiodan, bromopropylate, pirimiphos methyl, fenthion, prochloraz, pyridapenthion, malathion, chlorpyriphos, and imazalil.

The release modifying agent may be characterized based upon one or more of its reactivity, it composition, its physical structure, and the like. In some embodiments, a release modifying agent may include any of the following: adsorbents, absorbents, molecularly imprinted polymers (MIPS), non-molecularly imprinted polymers (NIPS), botanicals, antioxidants, chelating agents, cyclodextrins, and combinations thereof.

Absorbents can include any material subject to wetting and adapted to draw a releasable component into the structure thereof. Absorbents may particularly be porous articles, including fibrous materials, and may be specifically adapted to wicking of a liquid (e.g., saliva including a releasable component) into the structure thereof.

Adsorbents can include any material adapted for adhering a releasable component on a surface thereof (i.e., undergoing surface adsorption). Suitable adsorbents may exhibit physical adsorption and/or chemical adsorption. Non-limiting examples of adsorbents that may be suitable for use as a release modifying agent include activated carbon, activated aluminas, molecular sieves (including carbon molecular sieves and zeolites—e.g., aluminosilicates), clays, silica gels, ion exchange resins, and sodium bicarbonate.

Activated carbon can be particularly useful and preferably consists primarily of carbon—e.g., having a carbon content above about 80 weight percent, and more preferably above about 90 weight percent. Preferred carbonaceous materials are provided by carbonizing or pyrolyzing bituminous coal, tobacco material, softwood pulp, hardwood pulp, coconut shells, almond shells, grape seeds, walnut shells, macadamia shells, kapok fibers, cotton fibers, cotton linters, and the like. Carbon from almond shells, grape seeds, walnut shells, and macadamia nut shells are believed to provide greater vapor phase removal of certain compounds as compared to coconut shell carbon. Examples of suitable carbonaceous materials are activated coconut hull based carbons available from Calgon Corp. as PCB and GRC-11, coal-based carbons available from Calgon Corp. as S-Sorb, BPL, CRC-11F, FCA and SGL, wood-based carbons available from Westvaco as WV-B, SA-20 and BSA-20, carbonaceous materials available from Calgon Corp. as HMC, ASC/GR-1 and SC II, and Witco Carbon No. 637. Other carbonaceous materials are described in U.S. Pat. No. 4,771,795 to White, et al. and U.S. Pat. No. 5,027,837 to Clearman, et al.; and European Patent Application Nos. 236,922; 419,733 and 419,981; the disclosures of the foregoing being incorporated herein by reference.

A molecularly imprinted polymer (MIP) is a polymeric material that exhibits high binding capacity and selectivity for a specific target molecule or class of target molecules. MIPs comprise cavities that are engineered to selectively bind one or more target molecules. Unlike most separation particles that exhibit only non-selective interactions, MIPs have a selective recognition site, which is sterically and/or chemically complementary to a particular target molecule or class of structurally related target molecules. General discussion of MIPs is provided, for example, in Cormack et al., J. Chrom. B. 804:173-182 (2004); U.S. Pat. No. 5,630,978 to Domb; and US Pat. Appl. Pub. Nos. 2004/0157209 to Yilmaz et al., 2005/0189291 to Sellergren et al., and 2010/0113724 to Yilmaz et al., which are incorporated herein by reference. MIPs have been studied for the selective removal of various compounds from mixtures. For example, US Pat. Appl. Pub. Nos. 2010/0239726 to Pertsovich, 2008/0038832 to Sellergren et al.; and 2004/0096979 to Petcu et al., which are all incorporated herein by reference, describe methods of removing safrole, nitro-containing compounds, and phenols, respectively, from mixtures.

MIPs are typically prepared by copolymerizing functional monomers and crosslinkers in the presence of a "template" molecule that provides a three-dimensional outline around which the polymer is formed. The functional monomers organize around the template molecule and are then locked into position by polymerization with the crosslinkers and other functional monomers. The template molecule can be the target molecule or a structural analogue which mimics the target molecule. The template molecule directs the organization of the functional groups on the monomer units, and, following preparation of the polymer, the template molecule is removed from the MIP, providing cavities that are designed for the specific binding of a target compound.

Any method of polymer synthesis can be used to produce MIPs and NIPs. For example, cationic or anionic polymerization may be used. Free radical polymerization is the most commonly used method for the preparation of MIPs and NIPs. The preparation by free radical polymerization typically requires one or more monomers, one or more crosslinkers, one or more initiators, and, optionally, one or more solvents, in addition to the template molecule. Examples of monomers, crosslinkers, initiators, solvents, template molecules, and methods of preparation useful in forming MIPs and NIPs are described in U.S. Pat. No. 7,985,818 to Pertsovich and U.S. Pat. Pub. No. 2012/0291793 to Byrd et al., which are incorporated herein by reference. A MIP and/or a NIP, for example, may form at least a portion of the water-permeable fabric used to form the pouch, such as by utilizing fibers formed from the MIP and/or the NIP or by attaching the MIP and/or NIP to the fibers.

Botanical materials ("botanicals") refer to any plant material, including plant material in its natural form and plant material derived from natural plant materials, such as extracts or isolates form plant materials or treated plant materials (e.g., plant materials subjected to heat treatment, fermentation, or other treatment processes capable of altering the chemical nature of the material). For the purposes of the present disclosure, botanicals include but are not limited to "herbal materials," which refer to seed-producing plants that do not develop persistent woody tissue and are often valued for their medicinal or sensory characteristics (e.g., teas or tisanes). Reference to botanical material is not intended to include tobacco materials (i.e., does not include any *nicotiana* species). The botanical materials may comprise, without limitation, any of the compounds and sources set forth herein, including mixtures thereof. Certain botanical materials of this type are sometimes referred to as dietary supplements, nutraceuticals, "phytochemical s" or "functional foods."

Suitable botanicals particularly may exhibit antioxidant characteristics, and such botanicals may be particularly preferred, as well as non-botanical materials that exhibit antioxidant characteristics. Exemplary botanical materials, many of which are associated with antioxidant characteristics, include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, *Bacopa monniera*, *Withania somnifera*, and *Silybum marianum*.

Botanical materials often include compounds from various classes known to provide certain bioactive effects, such as minerals, vitamins such a ascorbic acid, isoflavones, phytoesterols, allyl sulfides, dithiolthiones, isothiocyanates, indoles, lignans, flavonoids, polyphenols, plant phenolics, tocopherols, ubiquinone, benzodioxoles, carotenoids, etc. Antioxidants obtained from botanicals can be classified in the following groups: monoterpenoid phenols; alcohols such as thymol, carvacol, menthol; p-cymene; diterpene phenols such as carnosic acid, carnosol, rosmanol; hydroxycinnamic type compounds such as caffeic acid, chlorogenic acid, rosmarinic acid, p-coumaric acid, resveratrol, curcumin, eugenol, cinnamaladehyde; hydroxybenzoic acids and derivatives such as gallic acid, protocatechuic acid, propyl gallate; 2-benzopryrones such as scopoletin, coumarin; 4-benzopyrones such as quercetin, genistein, naringenin, diosmin, rutin; dihydrochalcones such as aspalathin, notophagin; flavanols such as epicatechin, epigallocatechin, epicatechin gallate, epigallocatechin gallate; anthocyanins and anthocyanidins; triterpenes such as ursolic acid, oleanolic acid, betulinic acid, betulonic acid; tocopherols such as $\alpha$, $\beta$, $\gamma$, $\delta$-tocopherols; tocotrienols; carotenoids such as $\beta$-carotene or lutein; ubiquinone, CoQ10; ascorbyl palmitate; benzodioxoles such as myristicin, piperine, safrole; and other compounds such as gambogic acid, gingerol, and the like.

Exemplary compounds found in botanical materials include, but are not limited to, propylene glycol, lactic acid, glycolic acid, alanine, camphor, pyruvic acid, aspalathin, borneol, menthol, phosphate, glycerin, proline, succinic acid, thymol, glyceric acid, 2-butenedioic acid, 3-hydroxyglutaric acid, malic acid, 5-oxoproline (pyroglutamic acid), aspartic acid, trihydroxybutanoic acid, glutamine, asparagine, levoglucosan, xylitol, ribitol, 2-keto-L-gluconic acid, fructose, caffeine, citric acid, glucosamine, neophytadiene, altrose, quinic acid, xylulose, glucose, inositol, 2-amino-2- deoxyglucose, glucitol, ascorbic acid, glucose, gallic acid, gluconic acid, galactaric acid, hexadecanoic acid, 3,4-dihydroxyphenyl-2-hydroxypropionic acid, glucuronic acid, myoinositol, caffeic acid, tryptophan, linolenic acid, octadecanoic acid, galacturonic acid, rosmaricin, carnosic acid, melibiose, carnosol, phitosterol, sucrose, rosmanol, 2,5-deoxyfructosazine, 2,6-deoxyfructosazine, fructosazine, maltitol, epicatechin, nothofagin, orientin, catechin, epigallocatechin, coumaroyl quinic acid, tocoferol, chlorogenic acid, stigmasterol, rosmarinic acid, betulinic acid, oleanolic acid, ursolic acid, glyderinine, epicatechin gallate, catechin gallate, epigallocatechin gallate, gallocatechin gallate, solanesol, and the like. For additional exemplary compounds, see, e.g., Santhosh et al., Phytomedicine, 12 (2005) 216-220, which is incorporated herein by reference.

The botanical material can be used in the present pouched products in a variety of forms. Exemplary forms include plant materials in shredded or particulate (e.g., a milled or ground product in a form characterized as granular or powder) form. Exemplary forms also include isolated components of plant materials in forms such as oils, aqueous extracts, or alcohol (e.g., ethanol) extracts, which can be optionally used in solid form (e.g., freeze-dried or spray-dried form). Oils, aqueous extracts, and the like may be infused into the water-permeable fabric and/or may be encapsulated, in non-limiting embodiments. Botanicals, including botanically derived antioxidants, that may be useful according to the present disclosure are further described in U.S. patent application Ser. No. 14/072,318, filed Nov. 5, 2013, the disclosure of which is incorporated herein by reference.

A chelating agent is understood to be a ligand that is adapted for forming a chelate complex with a substrate. Chelating agents may be particularly useful as a release modifying agent for metal species. Non-limiting examples of chelating agents include dimercaprol or British anti-Lewisite (BAL); succimer or dimercaptosuccinic acid (DMSA); unithiol or 2,3-Dimercapto-1-propanesulfonic acid (DMPS); D-penicillamine (DPA); N-acetyl-D-penicillamine (NAPA); calcium disodium ethylenediaminetetraacetate (CaNa(2)EDTA); calcium trisodium or zinc trisodium diethylenetriaminepentaacetate (CaNa(3)DTPA, ZnNa(3) DTPA); deferoxamine (DFO); deferiprone; triethylenetetraamine or trientine; N-acetylcysteine (NAC); Prussian Blue (PB); and derivatives thereof.

Cyclodextrins are understood to be cyclic oligosaccharides composed of a number (e.g., 5 or greater) of α-D-glucopyranoside units. Non-limiting examples include α-cyclodextrin (6 units), β-cyclodextrin (7 units), and γ-cyclodextrin (8 units). Cyclodextrins can provide a hydrophilic interior with a hydrophobic exterior thus making the materials useful for forming a variety of complexes.

In some embodiments, a water-permeable fabric pouch as described herein can be characterized as comprising a filter media. In particular, a filter media can include any material that, under the specified conditions of use, is permeable to one or more components of a mixture, solution, or suspension, and is impermeable to the remaining components. As a non-limiting example, the nonwoven web forming the water-permeable fabric may be formed so as to be a filter media by nature of the porosity thereof, the fibers used in forming the web, and/or additives to the web (e.g., filter materials added to the web during formation thereof). In some embodiments, a release modifying agent in particulate form (e.g., an absorbent, adsorbent, MIP, NIP, or the like) may be included in the pouched product such that, under mouth conditions, the particulates substantially coat, or at least partially coat, the interior of the water-permeable fabric such that releasable components combined with saliva being withdrawn from the pouch may be modified in one or more release characteristics through reaction with the release modifying agent. In further embodiments, the water-permeable fabric may be infused with a composition (e.g., a botanical or other antioxidant) so that, under mouth conditions, the infused material functions to modify the release of releasable components that may otherwise pass through the water-permeable fabric. In these non-limiting examples, as well as further embodiments that may be envisioned in light of the present disclosure, the water-permeable fabric may substantially function to filter one or more releasable components—i.e., such that the one or more releasable components is not permeable to the water-permeable fabric while other materials (e.g., saliva and optionally some releasable components from the composition) are permeable to the water-permeable fabric. For example, under mouth conditions, first, second, and third releasable components may be released from the composition within the cavity of the water-permeable fabric pouch, such as by forming a solution with saliva, and while the saliva, the first releasable component, and the second releasable component may be permeable to the water-permeable fabric, the third releasable component may be non-permeable to the water-permeable fabric because of the presence of the release modifying agent and/or the nature of the water-permeable fabric otherwise as a filter media.

A water-permeable fabric useful according to the present disclosure may be formed of any material that provides the requisite water permeability so that releasable components may be released into the mouth and that still exhibits sufficient structure to retain the solid composition (e.g., power, particles, shredded material, or the like) inside the cavity defined by the fabric. The fabric particularly may be formed of fibers and more particularly may be formed of a nonwoven web of fibers. As used herein, the term "fiber" is defined as a basic element of textiles. Fibers are often in the form of a rope- or string-like element. As used herein, the term "fiber" is intended to include fibers, filaments, continuous filaments, staple fibers, and the like. The term "multicomponent fibers" refers to fibers that comprise two or more components that are different by physical or chemical nature, including bicomponent fibers. Specifically, the term "multicomponent fibers" includes staple and continuous fibers prepared from two or more polymers present in discrete structured domains in the fiber, as opposed to blends where the domains tend to be dispersed, random or unstructured.

The term "nonwoven" is used herein in reference to fibrous materials, webs, mats, batts, or sheets in which fibers are aligned in an undefined or random orientation. The nonwoven fibers are initially presented as unbound fibers or filaments. During manufacturing of the water-permeable fabric, fibers or filaments may be bound together. The manner in which the fibers or filaments are bound can vary, and include thermal, mechanical and chemical techniques that are selected in part based on the desired characteristics of the final product.

In some embodiments, a heat sealable binder coating may be utilized on the water-permeable fabric. In other embodiments, such coating may expressly be absent or reduced. Accordingly, in certain embodiments of the invention, the pouched product can be described as substantially free of a heat sealable binder coating. For example, the nonwoven web used to form the pouched product can comprise no more than about 0.5% by weight, no more than about 0.25% by weight, or no more than about 0.1% by weight (based on total weight of the nonwoven web) of a heat sealable binder coating. In some embodiments, the nonwoven web will be completely free of heat sealable binder coatings. As used herein, "heat sealable binder coatings" refers to liquid coating materials, such as acrylic polymer compositions, applied to a nonwoven web and which are capable of sealing seams of individual pouches upon heating.

In some embodiments, a fibrous nonwoven web useful in forming the water-permeable fabric can include a plurality of heat sealing binder fibers comprising a thermoplastic polymer capable of providing the function of heat sealing of the pouch. As used herein, a "binder fiber" can be a fiber of any type, size, chemistry, etc. that can be used for the purpose of undergoing softening or melting upon heating, such that the binder fiber can act as a binding agent for the nonwoven web. Nonwoven webs including heat sealing binder fibers are described in U.S. application Ser. No. 14/484,956, filed Sep. 12, 2014, the disclosure of which is incorporated herein by reference in its entirety.

A variety of fibers can be used to form a nonwoven "fleece" pouch—i.e., a water-permeable fabric. For example, cellulosic fibers (e.g., regenerated cellulose known as rayon or viscose fibers) can be used. In particular embodiments, the fibers can be staple fibers. Each fiber in the nonwoven web can be a homocomponent fiber; however, bicomponent fibers may be used in forming the nonwoven web. The water-permeable fabric can be formed of a single fiber type or may be formed of a plurality of fiber types. Further non-limiting examples of the types of fibers that can be used in forming the nonwoven web include those made of wool, cotton, fibers made of cellulosic material, such as regenerated cellulose, cellulose acetate, cellulose triacetate, cellulose nitrate, ethyl cellulose, cellulose acetate propionate, cellulose acetate butyrate, hydroxypropyl cellulose, methyl hydroxypropyl cellulose, protein fibers, and the like. See also, the fiber types set forth in US Pat. Appl. Pub. Nos. 2014/0083438 to Sebastian et al. and 2014/0026912 to Rushforth et al., which are incorporated herein by reference.

Regenerated cellulose fibers are particularly advantageous, and are typically prepared by extracting non-cellulosic compounds from wood, contacting the extracted wood with caustic soda, followed by carbon disulfide and then by sodium hydroxide, giving a viscous solution. The solution is subsequently forced through spinneret heads to create viscous threads of regenerated fibers. Exemplary methods for the preparation of regenerated cellulose are provided in U.S. Pat. No. 4,237,274 to Leoni et al; U.S. Pat. No. 4,268,666 to Baldini et al; U.S. Pat. No. 4,252,766 to Baldini et al.; U.S. Pat. No. 4,388,256 to Ishida et al.; U.S. Pat. No. 4,535,028 to Yokogi et al.; U.S. Pat. No. 5,441,689 to Laity; U.S. Pat. No. 5,997,790 to Vos et al.; and U.S. Pat. No. 8,177,938 to Sumnicht, which are incorporated herein by reference. The manner in which the regenerated cellulose is made is not limiting, and can include, for example, both the rayon and the TENCEL processes. Various suppliers of regenerated cellulose are known, including Lenzing (Austria), Cordenka (Germany), Aditya Birla (India), and Daicel (Japan).

The fibers used in the nonwoven web can vary and include fibers having any type of cross-section, including, but not limited to, circular, rectangular, square, oval, triangular, and multilobal. In certain embodiments, the fibers can have one or more void spaces, wherein the void spaces can have, for example, circular, rectangular, square, oval, triangular, or multilobal cross-sections. As noted previously, the fibers can be selected from single-component (i.e., uniform in composition throughout the fiber) or multicomponent fiber types including, but not limited to, fibers having a sheath/core structure and fibers having an islands-in-the-sea structure, as well as fibers having a side-by-side, segmented pie, segmented cross, segmented ribbon, or tipped multilobal cross-sections.

The physical parameters of fibers useful in forming a nonwoven web can vary. For example the fibers used in the nonwoven web can have varying size (e.g., length, dpf) and crimp characteristics. In some embodiments, fibers used in the nonwoven web can be nano fibers, sub-micron fibers, and/or micron-sized fibers. In certain embodiments, fibers useful herein can measure about 1.5 dpf to about 2.0 dpf, or about 1.6 dpf to about 1.90 dpf. In a preferred embodiment, each fiber can be a staple fiber. Each fiber length can measure about 35 mm to about 60 mm, or about 38 mm to about 55 mm, for example. In various embodiments, each fiber can measure about 4-10 crimps per cm, or about 5-8 crimps per cm. It is advantageous for all fibers in the nonwoven web to have similar fiber size and crimp attributes to ensure favorable blending and orientation of the fibers in the nonwoven web.

The means of producing the nonwoven web can vary. Web formation can be accomplished by any means known in the art. Web formation will typically involve a carding step, which involves deposition of the fibers (e.g., the heat sealable binder fibers and any additional fibers) onto a surface followed by aligning/blending the fibers in a machine direction. Thereafter, the nonwoven web is typically subjected to some type of bonding/entanglement including, but not limited to, thermal fusion or bonding, mechanical entanglement, chemical adhesive, or a combination thereof. In one embodiment, the nonwoven web is bonded thermally using a calendar (which can provide flat or point bonding), steam jet bonding, or a thru-air oven. Additional bonding methods include ultrasonic bonding and crimping. In some embodiments, needle punching is utilized, wherein needles are used to provide physical entanglement between fibers. In one embodiment, the web is entangled using hydroentanglement, which is a process used to entangle and bond fibers using hydrodynamic forces.

For example, in certain embodiments, the nonwoven web is made by a fleece carding process with point bonding. The point bonding (e.g., using a calendar) should be limited to a relatively small portion of the surface area of the nonwoven web to maintain good porosity in the web for migration of water-soluble components through the web during oral use. In certain embodiments, the point bonding is limited to less than about 60% of the surface area of the nonwoven web (or resulting pouch), such as less than about 50%, less than about 30%, or less than about 20% (e.g., about 1% to about 50%, about 5% to about 40%, or about 10% to about 30%). An advantage of point bonding is the ability to control the porosity, flexibility and fabric strength.

In other embodiments, the nonwoven web can be subjected to hydroentangling. The term "hydroentangled" or "spunlaced" as applied to a nonwoven fabric herein defines a web subjected to impingement by a curtain of high speed, fine water jets, typically emanating from a nozzle jet strip accommodated in a pressure vessel often referred to as a manifold or an injector. This hydroentangled fabric can be characterized by reoriented, twisted, turned and entangled fibers. For example, the fibers can be hydroentangled by exposing the nonwoven web to water pressure from one or more hydroentangling manifolds at a water pressure in the range of about 10 bar to about 1000 bar. As compared to point bonding, spunlace technology, in certain embodiments, will have less impact on porosity of the web and, thus, may enhance flavor transfer through the nonwoven pouch material.

In various embodiments, the nonwoven web can be subjected to a second bonding method in order to reduce elongation of the web during processing. In certain embodiments, carded and hydroentangled nonwoven webs of the invention can exhibit significant elongation during high speed processing on pouching equipment. Too much elongation of the nonwoven web can cause the web to shrink during processing, such that the final product is not sized appropriately. As such, it can be necessary to modify process equipment to fit a wider roll of fleece, for example, to compensate for any shrinkage in the final product due to elongation.

In order to avoid or at least reduce such an elongation problem, in various embodiments the nonwoven web can be point bonded after the first bonding (e.g., hydroentangling) is completed. A second bonding process can increase the tensile strength of the nonwoven web and reduce elongation characteristics. In particular, a point bonding process can bond a nonwoven web by partially or completely melting the web (e.g., the heat sealable binder fibers) at discrete points. For example, in some embodiments, the nonwoven web can be subjected to ultrasonic bonding after initial bonding of the web. Any ultrasonic bonding system for nonwoven materials known in the art can be used to ultrasonically bond the nonwoven web. See, for example, the apparatuses and devices disclosed in U.S. Pat. No. 8,096,339 to Aust and U.S. Pat. No. 8,557,071 to Weiler, incorporated by reference herein. In some embodiments, the nonwoven web can be subjected to point bonding via embossed and/or engraved calendar rolls, which are typically heated. See, e.g., the point bonding methods incorporating the use of very high calendar pressures and embossing techniques discussed in U.S. Pat. Publ. No. 2008/0249492 to Schmidt, herein incorporated by reference in its entirety. The point bonding process is typically limited to less than about 60% of the surface area of the nonwoven web as noted above.

In certain embodiments, product identifying information may be included on the water-permeable fabric pouch. In some embodiments, the product identifying information is selected from the group consisting of product brand, a company name, a corporate logo, a corporate brand, a marketing message, product strength, active ingredient, product manufacture date, product expiration date, product flavor, product release profile, weight, product code (e.g., batch code), other product differentiating markings, and combinations thereof. In particular embodiments, the processing techniques used to blend, entangle and bond the nonwoven web can also impart a desired texture to the fibrous nonwoven web material. For instance, point bonding or hydroentangling can impart a desired texture (e.g. a desired pattern) to the nonwoven web. This textured pattern can include product identifying information. Product identifying information may be included in further manners, such as described in U.S. Pub. No. US 2014/0255452 to Reddick et al., the disclosure of which is incorporated herein by reference.

The fibrous webs can have varying thicknesses, porosities and other parameters. The nonwoven web can be formed such that the fiber orientation and porosity of the pouched product formed therefrom can retain the composition adapted for oral use that is enclosed within the outer water-permeable pouch, but can also allow the flavors of the composition to be enjoyed by the consumer. For example, in some embodiments, the fibrous webs can have a basis weight of about 20 gsm to about 35 gsm, or about 25 gsm to about 30 gsm. In a preferred embodiment, the fibrous web can have a basis weight of about 28 gsm. Basis weight of a fabric can be measured using ASTM D3776/D3776M-09a (2013) (Standard Test Methods for Mass Per Unit Area (Weight) of Fabric), for example. In various embodiments, the fibrous web can have a thickness of about 0.1 mm to about 0.15 mm (e.g., about 0.11 mm). The fibrous web can have an elongation of about 70% to about 80%, e.g., about 78%. In some embodiments, the fibrous web can have a peak load of about 4 lbs. to about 8 lbs., e.g., about 5.5 lbs. Elongation and breaking strength of textile fabrics can be measured using ASTM D5034-09 (2013) (Standard Test Method for Breaking Strength and Elongation of Textile Fabrics (Grab Test)), for example. In various embodiments, the fibrous web can have a Tensile Energy Absorption (TEA) of about 35 to about 40, e.g., about 37. In certain embodiments, the fibrous web can have a porosity of greater than about 10,000 ml/min/cm$^2$. TEA can be measured, for example, as the work done to break the specimen under tensile loading per lateral area of the specimen. Porosity, or air permeability of textile fabrics can be measured using ASTM D737-04 (2012) (Standard Test method for Air Permeability of Textile Fabrics), for example.

In some embodiments, the water-permeable fabric can be made from a nonwoven web that is substantially a single layer web or fabric. In some embodiments, the water permeable fabric can be a multilayer composite made up of two or more nonwoven layers. Each nonwoven layer can be formed by processes discussed above. Multilayer structures that may be used according to the present disclosure are described in U.S. application Ser. No. 14/484,956, filed Sep. 12, 2014, which is incorporated herein by reference. In particular, a multilayer web can comprise a hydrophilic layer and a hydrophobic layer (compared to each other). The outer layer specifically may be hydrophilic, and the inner layer specifically may be hydrophobic. As such, the hydrophobic layer can, during storage of the pouched product, retain any moisture in the composition adapted for oral use such that flavors in the composition are not lost due to moisture loss. However, capillaries in the hydrophobic layer can wick out moisture into the mouth of the user, such that flavors are released into the oral cavity when used. In this manner, the pouch material can enhance storage stability without significantly compromising the enjoyment of the product by the end user. The two layers can be formed into a multi-layer composite nonwoven material using any means known in the art, such as by attaching the two layers together using adhesive or stitching. The hydrophobicity of a textile material can be evaluated, for example, by measuring the contact angles between a drop of liquid and the surface of a textile material, as is known in the art.

The hydrophilic and hydrophobic layers can be formed from similar nonwoven web compositions (e.g., both are constructed of a blend of viscose fibers with heat sealable binder fiber such as PLA fibers), but wherein one of the nonwoven webs is treated to enhance either hydrophobicity or hydrophilicity. For example, a layer of the nonwoven web can be treated with a wet chemical solution to confer hydrophilicity thereupon. In one such process, a nonwoven web layer is treated with an aqueous alcohol solution containing a food-grade surfactant. The surfactant may include, for example one or more of sorbitan aliphatic acid ester, polyglycerin aliphatic acid ester, or sucrose aliphatic acid ester (see, e.g., U.S. Pat. No. 7,498,281 to Iwasaki et al., which is incorporated herein by reference). In some embodiments, the fleece fabric layers can be made hydrophilic or hydrophobic by changing the cellulose fiber chosen. For example, predominantly hydrophobic cellulose fibers are commercially available as Tencel® Biosoft from Lenzing of Austria and as Olea Fiber from Kelheim of Germany. In various embodiments, the hydrophilic layer can incorporate cationic or anionic cellulose fibers that are also available from Kelheim of Germany, for example. The hydrophilic layer can contain additives such as polyethylene glycols, methyl cellulose, hydroxypropylmethyl cellulose, hydroxypropyl cellulose, hydroxypropylmethyl cellulose phthalate, polyvinyl pyrrolidone, polyvinyl alcohol, polyacrylic acids, gelatins, alginates, sulfosuccinates, and combinations thereof. Any of the exemplified fibers may be used in forming a single layer water-permeable fabric in some embodiments.

Various manufacturing apparatuses and methods can be used to create a pouched product described herein. For example, US Publication No. 2012/0055493 to Novak, III et al., previously incorporated by reference, relates to an apparatus and process for providing pouch material formed into a tube for use in the manufacture of smokeless tobacco products. Similar apparatuses that incorporate equipment for supplying a continuous supply of a pouch material (e.g., a pouch processing unit adapted to supply a pouch material to a continuous tube forming unit for forming a continuous tubular member from the pouch material) can be used to create a pouched product described herein. Representative equipment for forming such a continuous tube of pouch material is disclosed, for example, in U.S. Patent Application Publication No. US 2010/0101588 to Boldrini et al., which is incorporated herein by reference. The apparatus further includes equipment for supplying pouched material to the continuous tubular member such that, when the continuous tubular member is subdivided and sealed into discrete pouch portions, each pouch portion includes a charge of a composition adapted for oral use. Representative equipment for supplying the filler material is disclosed, for example, in U.S. Patent Application Publication No. US 2010/0018539 to Brinkley, which is incorporated herein by reference. In some instances, the apparatus may include a subdividing unit for subdividing the continuous tubular member into individual pouch portions and, once subdivided into the individual pouch portions, may also include a sealing unit for sealing at least one of the ends of each pouch portion. In other instances, the continuous tubular member may be sealed into individual pouch portions with a sealing unit and then, once the individual pouch portions are sealed, the continuous tubular member may be subdivided into discrete individual pouch portions by a subdividing unit subdividing the continuous tubular member between the sealed ends of serially-disposed pouch portions. Still in other instances, sealing (closing) of the individual pouch portions of the continuous tubular member may occur substantially concurrently with the subdivision thereof, using a closing and dividing unit.

An exemplary apparatus for manufacturing an oral pouch product is illustrated in FIGS. 1-5 of U.S. Publication No. 2012/0055493 to Novak, III et al.; however, this apparatus is used in a generic and descriptive sense only and not for purposes of limitation. It should also be appreciated that the following manufacturing process and related equipment is not limited to the process order described below. In various embodiments of the present invention, an apparatus similar to that described in U.S. Publication No. 2012/0055493 can be configured to removably receive a first bobbin on an unwind spindle assembly, the first bobbin having a continuous length of a material, such as a pouch material, wound thereon. When the first bobbin is engaged with the apparatus, the pouch material can be routed from the first bobbin to a forming unit configured to form a continuous supply of the pouch material into a continuous tubular member defining a longitudinal axis.

As such, as the pouch material is unwound from the first bobbin, the pouch material can be directed around an arrangement of roller members, otherwise referred to herein as a dancer assembly. A forming unit can be configured to cooperate with the first bobbin and the dancer assembly to take up slack in the pouch material and to maintain a certain amount of longitudinal tension on the pouch material as the pouch material is unwound from the first bobbin and fed to the forming unit, for example, by a drive system. One of ordinary skill in the art will appreciate that, between the first bobbin and the forming unit, the pouch material can be supported, routed, and/or guided by a suitably aligned series of any number of, for example, idler rollers, guideposts, air bars, turning bars, guides, tracks, tunnels, or the like, for directing the pouch material along the desired path. Typical bobbins used by conventional automated pouch making apparatuses often contain a continuous strip of pouch material of which the length may vary. As such, the apparatus described herein can be configured so as to handle bobbins of that type and size.

The forming unit can include one or more roller members configured to direct the pouch material about a hollow shaft such that the continuous supply of the pouch material can be formed into a continuous tubular member. The forming unit can include a sealing device configured to seal, fix, or otherwise engage lateral edges of the pouch material to form a longitudinally-extending seam, thereby forming a longitudinally-extending continuous tubular member. In various embodiments, an insertion unit can be configured to introduce charges of the composition adapted for oral use into the continuous tubular member through the hollow shaft. The insertion unit may be directly or indirectly engaged with the hollow shaft.

A leading edge or end (also referred to as a laterally-extending seam) of the continuous tubular member can be closed/sealed such that a charge of composition adapted for oral use inserted by the insertion unit, is contained within the continuous tubular member proximate to the leading end. The leading end can be closed/sealed via a closing and dividing unit configured to close/seal a first portion of the continuous tubular member to form the closed leading end of a pouch member portion. The closing and dividing unit can also be configured to form a closed trailing edge or end of a previous pouch member portion. In this regard, the closing and dividing unit can also be configured to close a second portion of the continuous tubular member to form the closed trailing end of the pouch member portion. In this regard, the closing and dividing unit can close the ends, by heat-sealing, or other suitable sealing mechanism.

As discussed above, a binder coating is not necessary for embodiments of the present invention. Instead, a heat sealable binder fiber incorporated into the nonwoven web of the pouch material can act as a heat sealable binder to seal the pouch once the composition adapted for oral use is inserted within the outer water-permeable pouch.

As illustrated in FIGS. 20-22 of U.S. Publication No. 2012/0055493 to Novak, III et al., the closing and dividing unit can be configured to divide the continuous tubular member, between the closed trailing end and the closed leading end of serially-disposed pouch member portions, along the longitudinal axis of the continuous tubular member, and into a plurality of discrete pouch member portions such that each discrete pouch member portion includes a portion of the oral composition from the insertion unit. In this regard, the closing and dividing unit can include a blade, heated wire, or other cutting arrangement for severing the continuous tubular member into discrete pouch member portions. For example, the closing and dividing unit can include first and second arm members configured to interact to close and divide the continuous tubular member.

In operation, a charge of the composition adapted for oral use (i.e., an amount suitable for an individual pouch member portion) can be supplied to the pouch member portion by an insertion unit after a leading end has been closed, but prior to the closing of a trailing end. In various embodiments, after receiving the charge of the oral composition, the discrete individual pouch member portion can be formed by closing the trailing end and severing the closed pouch member portion from the continuous tubular member such that an individual pouched product is formed.

The amount of material contained within each pouch may vary. In smaller embodiments, the dry weight of the material within each pouch is at least about 50 mg to about 150 mg. For a larger embodiment, the dry weight of the material within each pouch preferably does not exceed about 300 mg to about 500 mg. In some embodiments, each pouch/container may have disposed therein a flavor agent member, as described in greater detail in U.S. Pat. No. 7,861,728 to Holton, Jr. et al., which is incorporated herein by reference. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In various embodiments, the nonwoven web can be sufficiently tacky so as to create issues with high-speed pouching equipment. Therefore, in certain embodiments, a Teflon coating, or similar material, can be applied to one or more surfaces of the pouching equipment that touch the nonwoven web such as, for example, rollers, cutting instruments, and heat sealing devices in order to reduce and/or alleviate any problems associated with the pouch material sticking to the pouching equipment during processing.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A pouched product adapted for oral use, comprising:
  a water-permeable fabric pouch formed so as to define a cavity therein;
  a composition contained within the cavity of the water-permeable fabric pouch, the composition comprising one or more releasable components that are released from the composition under mouth conditions and that are capable of movement through the water-permeable fabric pouch, the composition comprising nicotine and at least one particulate non-tobacco material; and
  at least one capsule contained within the cavity of the water-permeable fabric pouch, the at least one capsule having a capsule wall surrounding an inner payload comprising at least one botanical.

2. The pouched product of claim 1, wherein the capsule wall comprises a material configured to be broken by shear forces.

3. The pouched product of claim 1, wherein the at least one particulate non-tobacco material comprises microcrystalline cellulose.

4. The pouched product of claim 1, wherein the nicotine is synthetic nicotine.

5. The pouched product of claim 4, wherein the synthetic nicotine is in the form of S(−)-nicotine or a racemic mixture composed predominantly of S(−)-nicotine.

6. The pouched product of claim 1, wherein the fabric pouch is formed of a nonwoven web of fibers.

7. The pouched product of claim 6, wherein the nonwoven web has a basis weight of about 20 gsm to about 35 gsm.

8. The pouched product of claim 6, wherein the nonwoven web has an elongation of about 70% to about 80%.

9. The pouched product of claim 1, wherein the composition further comprises at least one buffer or pH control agent.

10. The pouched product of claim 9, wherein the at least one buffer or pH control agent is selected from the group consisting of magnesium oxide, magnesium hydroxide, potassium carbonate, sodium carbonate, potassium bicarbonate, sodium bicarbonate, and mixtures thereof.

11. The pouched product of claim 1, wherein the composition further comprises at least one natural or artificial sweetener.

12. The pouched product of claim 11, wherein the at least one natural or artificial sweetener is selected from the group consisting of saccharin, acesulfame K, aspartame, sucralose, isomalt, lactose, mannitol, sorbitol, xylitol, and sucrose.

13. The pouched product of claim 1, wherein the composition further comprises at least one binder.

14. The pouched product of claim 1, wherein the at least one botanical is in the form of an oil, an aqueous extract, or an alcohol extract.

15. The pouched product of claim 1, wherein the at least one botanical comprises at least one compound selected from the group consisting of propylene glycol, lactic acid, glycolic acid, alanine, camphor, pyruvic acid, aspalathin, borneol, menthol, phosphate, glycerin, proline, succinic acid, thymol, glyceric acid, 2-butenedioic acid, 3-hydroxyglutaric acid, malic acid, 5-oxoproline (pyroglutamic acid), aspartic acid, trihydroxybutanoic acid, glutamine, asparagine, levoglucosan, xylitol, ribitol, 2-keto-L-gluconic acid, fructose, caffeine, citric acid, glucosamine, neophytadiene, altrose, quinic acid, xylulose, glucose, inositol, 2-amino-2-deoxyglucose, glucitol, ascorbic acid, glucose, gallic acid, gluconic acid, galactaric acid, hexadecanoic acid, 3,4-dihydroxyphenyl-2-hydroxypropionic acid, glucuronic acid, myoinositol, caffeic acid, tryptophan, linolenic acid, octadecanoic acid, galacturonic acid, rosmaricin, carnosic acid, melibiose, carnosol, phitosterol, sucrose, rosmanol, 2,5-deoxyfructosazine, 2,6-deoxyfructosazine, fructosazine, maltitol, epicatechin, nothofagin, orientin, catechin, epigallocatechin, coumaroyl quinic acid, tocoferol, chlorogenic acid, stigmasterol, rosmarinic acid, betulinic acid, oleanolic acid, ursolic acid, glyderinine, epicatechin gallate, catechin gallate, epigallocatechin gallate, gallocatechin gallate, and solanesol.

16. The pouched product of claim 1, wherein the at least one botanical comprises at least one compound selected from the group consisting of vitamins, isoflavones, phytoesterols, allyl sulfides, dithiolthiones, isothiocyanates, indoles, lignans, flavonoids, polyphenols, plant phenolics, tocopherols, ubiquinone, benzodioxoles, and carotenoids.

17. The pouched product of claim 1, wherein the at least one botanical comprises at least one compound selected from the group consisting of monoterpenoid phenols, alcohols, diterpene phenols, hydroxycinnamic-type compounds, hydroxybenzoic acids, 2-benzopryrones, 4-benzopyrones, dihydrochalcones, flavanols, anthocyanins, anthocyanidins, triterpenes, tocopherols, tocotrienols, carotenoids, ubiquinone, CoQ10, ascorbyl palmitate, benzodioxoles, gambogic acid, and gingerol.

18. The pouched product of claim 1, wherein the at least one botanical comprises at least one compound selected from the group consisting of monoterpenoid phenols, diterpene phenols, triterpenes, eugenol, polyphenols, carvacol, menthol, and ascorbic acid.

19. The pouched product of claim 1, wherein the at least one botanical is selected from the group consisting of acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints, oolong tea, beet root, orange, oregano, papaya, pennyroyal, peppermint, red clover, rooibos, rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, *Bacopa monniera*, *Withania somnifera*, and *Silybum marianum*.

20. The pouched product of claim 1, wherein the at least one botanical is spearmint or peppermint.

21. The pouched product of claim 1, wherein the at least one capsule has a diameter of about 0.5 mm to about 5 mm.

22. The pouched product of claim 1, wherein the capsule wall comprises carrageenan.

23. A pouched product adapted for oral use, comprising:
    a water-permeable fabric pouch formed so as to define a cavity therein;
    a composition contained within the cavity of the water-permeable fabric pouch, the composition comprising one or more releasable components that are released from the composition under mouth conditions and that are capable of movement through the water-permeable fabric pouch, the composition comprising synthetic nicotine, microcrystalline cellulose, at least one natural or artificial sweetener, and sodium bicarbonate; and
    at least one capsule contained within the cavity of the water-permeable fabric pouch, the at least one capsule having a capsule wall surrounding an inner payload comprising at least one botanical, wherein the at least one botanical comprises at least one compound selected from the group consisting of monoterpenoid phenols, diterpene phenols, triterpenes, eugenol, polyphenols, carvacol, menthol, and ascorbic acid.

* * * * *